United States Patent
Lubatschowski et al.

(10) Patent No.: US 12,153,286 B2
(45) Date of Patent: Nov. 26, 2024

(54) DEVICE AND METHOD FOR CREATING AN APERTURE DIAPHRAGM IN AN INTRAOCULAR LENS

(71) Applicant: ROWIAK GMBH, Hannover (DE)

(72) Inventors: Holger Lubatschowski, Hannover (DE); Georg Gerten, Bonn (DE)

(73) Assignee: ROWIAK GMBH, Hannover (DE)

(*) Notice: Subject to any disclaimer, the term of this patent is extended or adjusted under 35 U.S.C. 154(b) by 630 days.

(21) Appl. No.: 17/263,968

(22) PCT Filed: Jul. 30, 2019

(86) PCT No.: PCT/EP2019/070510
§ 371 (c)(1),
(2) Date: Jan. 28, 2021

(87) PCT Pub. No.: WO2020/025616
PCT Pub. Date: Feb. 6, 2020

(65) Prior Publication Data
US 2021/0311324 A1    Oct. 7, 2021

(30) Foreign Application Priority Data
Aug. 1, 2018 (DE) ............ 10 2018 118 714.9

(51) Int. Cl.
G02C 7/02 (2006.01)
A61F 2/16 (2006.01)
G02C 7/06 (2006.01)

(52) U.S. Cl.
CPC ............... *G02C 7/024* (2013.01); *A61F 2/16* (2013.01); *G02C 7/06* (2013.01); *A61F 2240/001* (2013.01)

(58) Field of Classification Search
CPC ... G02C 7/024; G02C 7/06; A61F 2/16; A61F 2240/001
(Continued)

(56) References Cited

U.S. PATENT DOCUMENTS 4,955,904 A    9/1990    Atebara et al.
5,757,458 A    5/1998    Miller et al.
(Continued)

FOREIGN PATENT DOCUMENTS

CN    101404951    4/2009
CN    101977575    2/2011
(Continued)

OTHER PUBLICATIONS

Alio, Jorge L.; et al., "Removability of a small aperture intracorneal inlay for presbyo-pia correction," Journal of refractive surgery 29 (8), pp. 550-556 (2013).

*Primary Examiner* — Sharrief I Broome
(74) *Attorney, Agent, or Firm* — PRICE HENEVELD LLP (57) ABSTRACT

A device for correcting or mitigating refractive errors in the eye presents a solution in which desired improvements in eyesight are achieved as far as possible without limiting everyday activities and where performing the treatment itself involves minimum risk. The device creates an aperture diaphragm in an eye, and has a control unit for a laser unit, the control unit being designed to control the laser unit to create the aperture diaphragm in a lens of the eye, wherein the aperture diaphragm is used to increase the depth of focus of the eye and is formed by laser-induced lesions which reduce light transmission through a lens aperture region surrounding an aperture opening.

14 Claims, 6 Drawing Sheets

(58) Field of Classification Search
USPC .................................................. 359/159, 0.74
See application file for complete search history.

(56) References Cited

U.S. PATENT DOCUMENTS

| | | | |
|---|---|---|---|
| 5,980,040 | A | 11/1999 | Xu et al. |
| 6,905,641 | B2 | 6/2005 | Platt et al. |
| 2009/0137988 | A1 | 5/2009 | Kurtz |
| 2009/0281620 | A1* | 11/2009 | Sacharoff ............... A61F 2/1635 623/6.22 |
| 2010/0004641 | A1 | 1/2010 | Frey et al. |
| 2010/0004643 | A1* | 1/2010 | Frey ................. A61F 9/008 606/5 |
| 2010/0228345 | A1 | 9/2010 | Bille |
| 2011/0118712 | A1 | 5/2011 | Lubatschowksi et al. |
| 2011/0172649 | A1* | 7/2011 | Schuele ................ A61F 9/008 606/4 |
| 2013/0103012 | A1* | 4/2013 | Grant .................. A61F 9/00834 606/5 |
| 2013/0131795 | A1 | 5/2013 | Miller et al. |
| 2013/0289543 | A1* | 10/2013 | Mordaunt ............. A61F 2/1613 606/5 |
| 2014/0058367 | A1 | 2/2014 | Dantus |
| 2015/0335477 | A1 | 11/2015 | Schuele et al. |
| 2016/0074967 | A1 | 3/2016 | Sahler et al. |
| 2017/0181846 | A1 | 6/2017 | Knox et al. |
| 2018/0177639 | A1 | 6/2018 | Rao et al. |

FOREIGN PATENT DOCUMENTS

| | | |
|---|---|---|
| CN | 103930016 | 7/2014 |
| EP | 2231084 | 9/2010 |
| EP | 2468226 | 6/2012 |
| KR | 20140104584 | 8/2014 |
| WO | 2011020078 | 2/2011 |
| WO | 2017221068 | 6/2017 |

* cited by examiner

DEVICE AND METHOD FOR CREATING AN APERTURE DIAPHRAGM IN AN INTRAOCULAR LENS

CROSS-REFERENCE TO FOREIGN PRIORITY APPLICATION

The present application claims the benefit under 35 U.S.C. §§ 119(b), 119(e), 120, and/or 365(c) of PCT/EP2019/070510 filed Jul. 30, 2019, which claims priority to German Application No. 102018118714.9 filed Aug. 1, 2018.

FIELD OF THE INVENTION

The present invention relates to the field of devices for correcting or mitigating refractive errors in the eye and, in particular, to a device for creating an aperture diaphragm in an intraocular lens (IOL) (implanted) in an eye, with which the depth of focus of the eye is increased. This is particularly useful for improving the near-vision acuity of an eye into which a monofocal IOL has been implanted.

BACKGROUND OF THE INVENTION

A refractive error of the (natural) eye is generally remedied by spectacles or contact lenses. In cases of ametropia, an object at optical infinity is not imaged sharply on the retina when the ciliary muscle is relaxed (distance accommodation). When the eyeball is too long in comparison with the total refractive power of the cornea and lens, this is referred to as myopia (near-sightedness or short-sightedness). Glasses or contact lenses that act as a diverging lens can reduce the refractive power so that a sharp image is formed on the retina. In the converse case of hyperopia (long-sightedness), the refractive power of the eye media is too small in relation to the eyeball length. In this case, a converging lens in the form of glasses or a contact lens can correct the refractive error. If the refractive error is in one plane only, this is referred to as astigmatism. Appropriate cylindrical lenses, likewise in the form of glasses or contact lenses, can correct this refractive error.

In addition to glasses or contact lenses as corrective aids, there are surgical procedures for correcting refractive errors of the eye.

Parts of the cornea can be removed using lasers, thus modifying the anterior curvature of the cornea in such a way that the optical refractive power of the eye is changed accordingly, and (approximately) normal vision (emmetropia) is achieved. One advantage of such laser procedures (PRK: photorefractive keratectomy, LASIK: laser-assisted in-situ keratomileusis, LASEK: Laser epithelial keratomileusis) derives from the flexibility of the correction to be achieved. Corneal irregularities can be corrected in a targeted manner, which is often not possible with glasses and contact lenses.

It is also possible to insert implants into the cornea, the aim of which is to correct the specific refractive error by means of their optical refractive power or their biomechanical effect (for example, by modifying the curvature of the cornea).

Intraocular lenses can also be implanted into the eye to correct refractive errors. These can act in addition to the natural lens of the eye, or replace the natural lens of the eye.

A cataract is an eye disease due to aging, in which the natural lens of the eye becomes cloudy and loses transparency. In most cases, such clouded lenses are surgically removed from the eye and replaced with an artificial lens implant (intraocular lens (IOL)). Such operations are some of the most frequently performed surgical procedures.

A lens which is still clear and unclouded can also be replaced with an IOL in cases of severe short-sightedness or long-sightedness, or when there is a complete loss of accommodation. This is called refractive lens exchange (RLE) in such cases.

After removal of the natural lens, the eye can no longer adjust (accommodate) to different visual distances. In most cases, the IOL is calculated in such a way that optimal distance vision is possible. Reading glasses are then required for near vision (e.g., for reading). "Accommodative" intraocular lenses, which focus the image sharply on the retina for a desired distance, like natural lenses, are a subject of current research. However, satisfactory results are not yet known. "Multifocal" intraocular lenses offer the possibility of largely dispensing with spectacles by producing two or more points of focus, such that objects at a distance, in the intermediate range and nearby are sharply and proportionately imaged on the retina. The disadvantage of such lenses is that weak double images are produced and that a decrease in contrast sensitivity must be accepted. IOLs with extended depth of focus (EDOF) work in a similar manner and produce an elongated focal point, due to their external shape and thus their refractive power, in order to increase the depth of focus.

Implant solutions also include a group of implants which make use of the principle of the stenopeic hole (pinhole effect). The pinhole reduces interfering marginal rays, thus reducing spherical aberrations in imaging. The circles of confusion on the retina are made smaller, thus increasing the depth of focus in imaging. Ametropic eyes consequently acquire greater visual acuity when looking through a pinhole aperture. This approach can also be used to enable or improve reading ability after implantation of an IOL, without having to wear glasses. When the depth of focus is increased, one is able to see near and distant objects in sharp focus, even with a non-accommodating eye (e.g., with a monofocal IOL).

In one variant of such an approach relating to the natural eye, a plastic disc approximately 5 μm thick, with an open internal diameter of approximately 1.6 mm and an external diameter of 3.8 mm, is centrally inserted into the cornea of the eye. This is mostly done operatively by using a laser to create a pocket in the cornea, into which the implant is fixated.

Figure 2A:
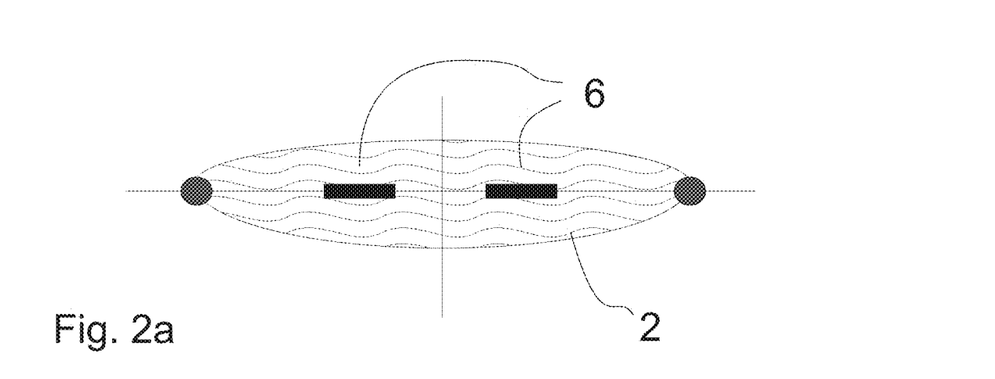
FIGS. 2a and 2b show schematic views of an intraocular lens with an aperture.
Figure 2B:
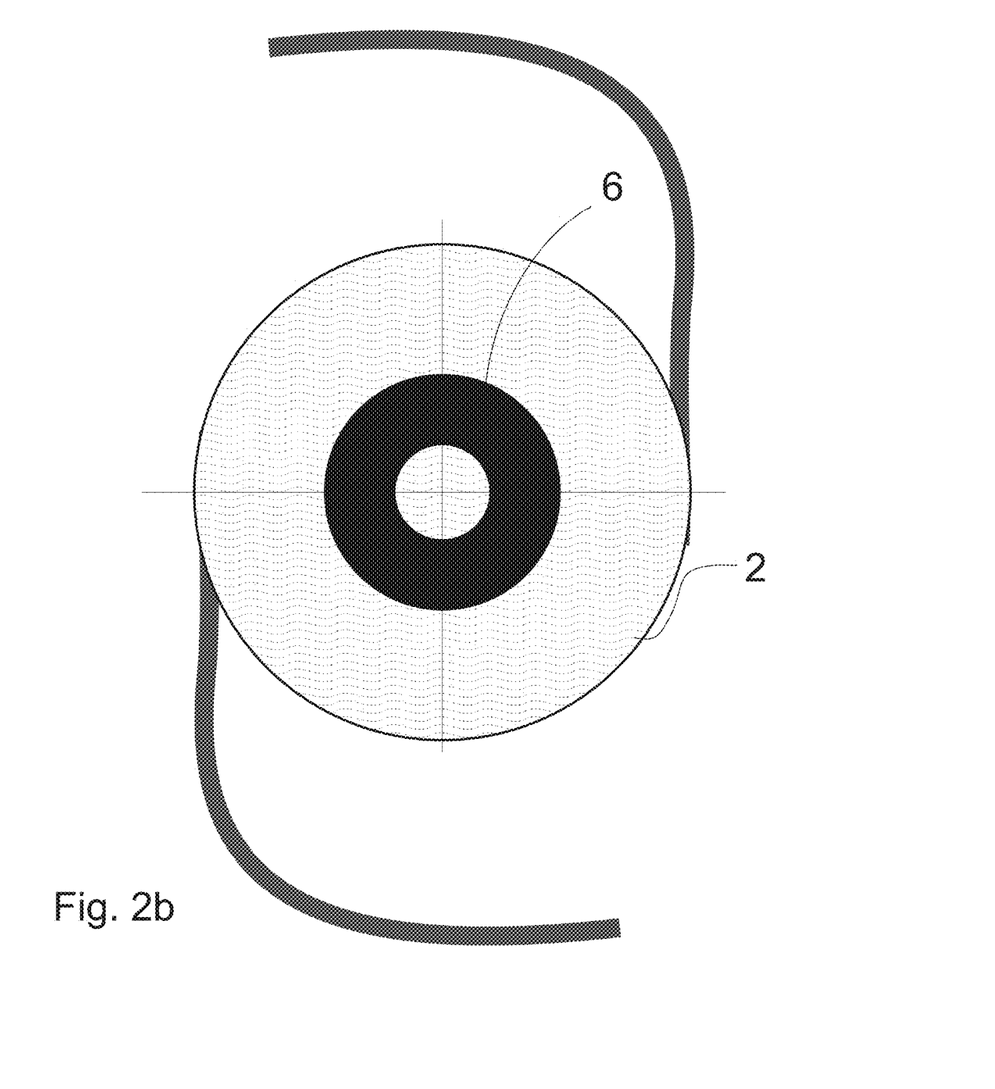

In another variant, an artificial intraocular lens (IOL) is implanted into the eye. The natural lens is removed in the process. Inside the artificial lens, there is likewise a pinhole aperture with an open internal diameter of approximately 1.36 mm and an external diameter of 3.23 mm, as illustrated in FIGS. 2a and 2b, in which reference sign 2 denotes the IOL and reference sign 6 denotes the pinhole or aperture. As artificial intraocular lenses (IOL) in general are known from the prior art, as are those, in particular, which are provided with a pinhole or aperture, an in-depth description of further details can be dispensed with here.

Finally, the pinhole effect can also be utilized with the aid of a contact lens. However, contact lenses can generally move easily on the cornea. The central opening is moved out of the visual axis, thus impairing optimal vision.

Examples from the prior art which relate to utilization of the pinhole effect can be found, for example, in U.S. Pat. Nos. 4,955,904, 5,757,458, 5,980,040, WO 2011/020078 A1 and US 2013/131795 A1.

Figure 1A:
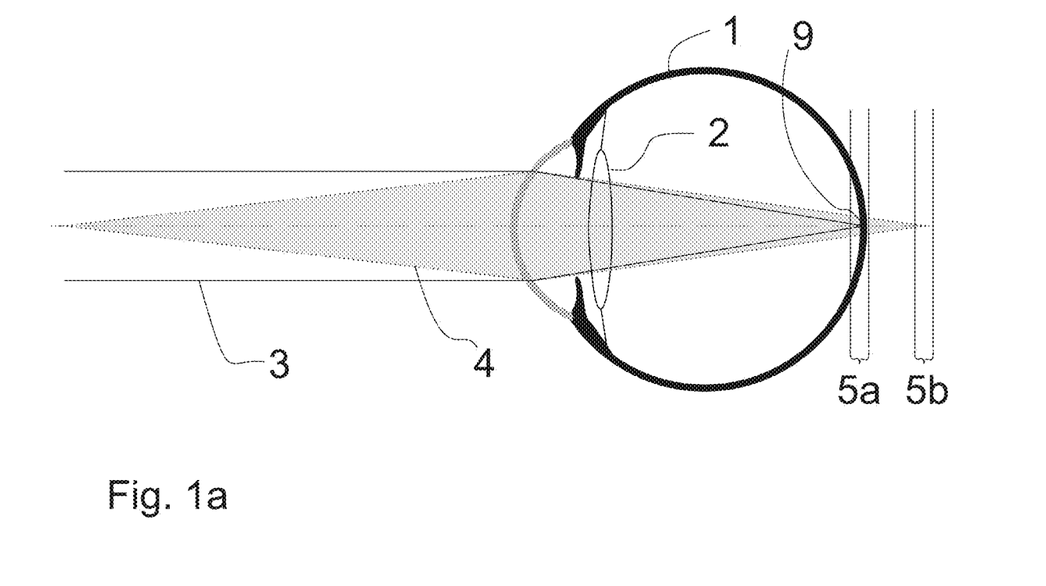
FIGS. 1a and 1b show schematic views for describing the depth of focus and the effect of a depth of focus which has been increased by means of a pinhole aperture.
Figure 1B:
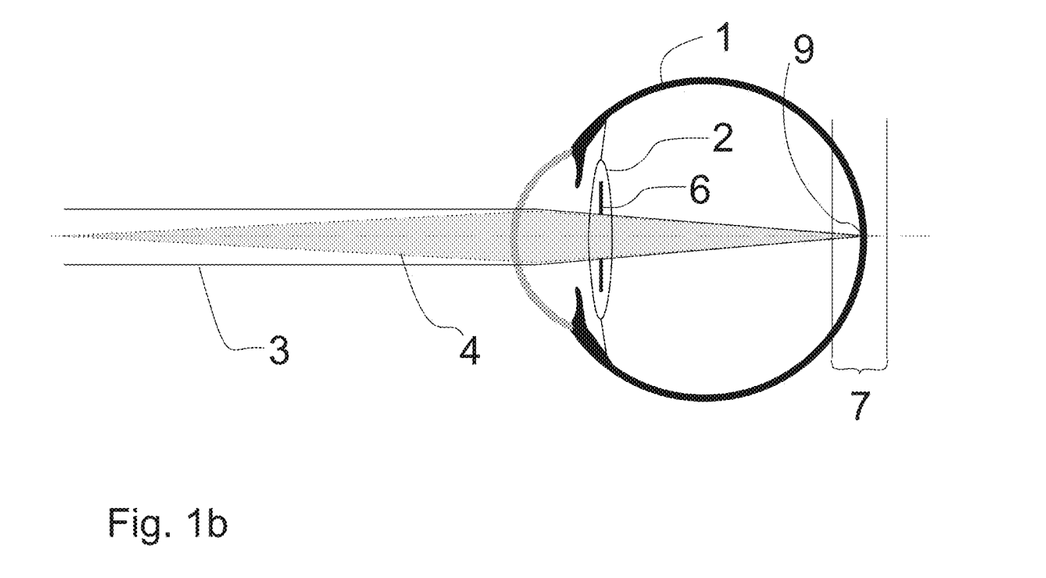

The purpose of the illustrations in FIGS. 1a and 1b is to show clearly the increased depth of focus effect that results when a pinhole 6 is introduced. An IOL 2 optimized for distance vision and implanted in eye 1 focuses a parallel incident beam from distance 3 onto the retina of the eye 9 with a short depth of focus 5a. Due to the insufficient refractive power of IOL 2, the light from an object at close range 4 is imaged behind retina 9 with a similarly short depth of focus 5b.

If the entrance opening for the incident light 3 and 4 is constricted by an aperture 6, the depth of focus 7 for imaging is so wide, if aperture 6 is suitably dimensioned, that sufficiently sharp imaging on retina 9 occurs both for near objects 4 and for light 3 incident from a distance.

In everyday life, glasses can be damaged or lost. Depending on the surroundings, they can become dirty or can mist up. Irregular refractive errors, other than myopia, hyperopia or astigmatism can be corrected only to an inadequate extent or not at all, and this is also the case with contact lenses, which additionally require a certain amount of dexterity when inserting and removing them.

Surgical procedures using laser and implants involve risks of infection during and after the operation and/or of tissue intolerance to the implant. Inserting the pinhole implant in the cornea is known to have adverse effects on the supply of nutrients to the tissue (Alio, Jorge L.; et al. (2013): Removability of a small aperture intracorneal inlay for presbyopia correction. in: Journal of refractive surgery 29 (8), pp. 550-556).

As indicated above, however, there are indeed situations where there is currently no known workaround for using an implant while simultaneously maintaining (or restoring) visual acuity.

IOLs are generally implanted in the residual capsular bag of the natural lens. In some cases, positioning of the IOL is not done optimally. What also happens in some cases is that, even when the IOL is well positioned, the capsular bag and the zonular fibers holding it in position change their shape postoperatively, thus causing the IOL to be moved to a new position. In that case, the imaging elements of the eye (cornea, pupil, IOL, macula) are no longer aligned along an axis, and the image quality is reduced accordingly.

With the aid of artificial "light-adjustable lenses" (LAL), postoperative attempts are made to change the shape and refractive power of the implanted IOL by illuminating it with UV light, for example, in order to correct refractive errors and positioning errors after cataract surgery. However, such a lens requires special materials that react to UV light.

In another procedure, ultrashort pulses can be used to produce a change or changes in the refractive index of the IOL material. Optical modifications of the lens can also be carried out subsequently in this way. In a typical embodiment, concentric ring structures are created that partially or completely change the refractive power of the IOL, based on the principle of diffractive optics or the principle of Fresnel's zone plate.

Changing the refractive index by means of ultrashort laser pulses can be carried out on conventional IOL materials in some cases. This is based on nonlinear absorption (multiphoton absorption) of the laser pulses in the transparent IOL. This generates free electrons where the laser light is focused, which, in turn, triggers local chemical reactions that directly or indirectly change the optical refractive index of the material. However, the material as a whole remains transparent and is not destroyed.

The disadvantage of this method, however, is that positioning the laser focus requires a very high level of accuracy. Particularly when creating diffractive structures within the IOL, positioning accuracies in the order of magnitude of the wavelength of the light are necessary. This requirement poses a major technical challenge when a lens implanted in the patient's eye is involved.

More detailed descriptions of embodiments utilizing the subsequent change of the refractive index of the implanted IOL can be found, for example, in U.S. Pat. No. 6,905,641, US 2016/074967 A1, WO 2017/221068 A1 and US 2017/181846 A1.

A particular objective of the present invention is to allow the depth of focus of implanted IOLs to be increased, in order to restore or at least to improve the reading ability of the eye. An additional or further object is to correct visual defects caused by aberrations, in particular, in the periphery of the optical axis of the eye, by masking the marginal rays of the light entering the eye. The disadvantages of the prior art are to be avoided completely or at least substantially thereby.

It is, therefore, desired that a solution be presented with which the desired improvements in visual acuity are achieved, as far as possible without additional restrictions with regard to the choice of material, for example, or excessive requirements in respect of positioning and accuracy, and which also involves as little risk as possible when performing the treatment itself, in particular, so that there is no need for any further invasive actions (such as re-opening of the eye, or the introduction of substances (e.g., dyes, pigments) into the eye).

SUMMARY OF THE INVENTION

According to a first aspect of the invention, a device for creating an aperture diaphragm in an artificial intraocular lens implanted into an eye is provided, said device comprising a control unit for a laser unit, wherein the control unit is designed to control the laser unit to create the aperture diaphragm in said intraocular lens, wherein the aperture diaphragm is used to increase the depth of focus of the eye and is formed by laser-induced modification of the material of the intraocular lens, which reduces light transmission through an intraocular lens aperture region surrounding an aperture opening, wherein the control unit is designed to control the laser unit in such a way that creation of the aperture diaphragm starts from a predetermined nucleation zone in the intraocular lens.

Other aspects of the invention relate to: an intraocular lens for implanting into an eye, said intraocular lens having a predetermined nucleation zone, wherein the nucleation zone is designed for linear absorption of energy delivered by laser; a method of generating control commands for a laser unit for creating an aperture diaphragm in an intraocular lens implanted in an eye, wherein the control commands cause the laser unit to create the aperture diaphragm in the intraocular lens, wherein the aperture diaphragm is used to increase the depth of focus of the eye and is formed by laser-induced modification of the material of the intraocular lens, which reduces light transmission through an intraocular lens aperture region surrounding an aperture opening, wherein the control commands cause the laser unit to control the laser unit in such a way for creation of the aperture diaphragm that creation of the aperture diaphragm starts from a predetermined nucleation zone in the intraocular lens; a method of creating an aperture diaphragm in an artificial intraocular lens implanted into an eye, said method comprising the step of controlling a laser unit to create the aperture diaphragm in a lens of the eye, wherein the aperture diaphragm is used to increase the depth of focus of the eye and is formed by laser-induced modification of the material of the intraocular lens, which reduces light transmission through an intraocular lens aperture region surrounding an aperture opening, wherein the laser unit is controlled in such a way that creation of the aperture diaphragm starts from a predetermined nucleation zone in the intraocular lens, and a computer program comprising programming means which cause a device according to the invention to perform a method of creating an aperture diaphragm in an artificial intraocular lens implanted into an eye, when the computer program is executed on the device.

According to the invention, an aperture (pinhole) is created in an IOL which has already been implanted into the eye. The aperture is created without surgically opening the eye. The IOL already implanted may be of any material, as implanted at the time in accordance with the state of the art, or as previously implanted. This notwithstanding, an IOL may also be used whose material is particularly suitable for creating an aperture after insertion of the IOL.

Since the invention allows the aperture to be applied in a non-invasive manner (in the sense that there is no further opening of the eye once the IOL has been inserted), a sterile environment (operating theatre) is not required to create the aperture. Nor is it specified that substances (dyes, pigments) be introduced into the eye, so no intolerances or the like are to be feared in that respect, either.

The aperture is preferably created at a time when the previously operated eye has (re)stabilized following implantation of an IOL. It is advantageous, in particular, if the positioning of the IOL is stable, which means, for example, that the capsular bag in which the IOL is located and the adjoining zonular fibers keep a stable form, and that there is no change or only marginal change in the position of the IOL. This is typically the case three months after the IOL has been implanted.

An aperture that is subsequently and non-invasively inserted into a stable eye also allows the size of the aperture opening (i.e., the central, light-transmitting part of the mask), for example, to be advantageously adjusted to optical needs. By varying the size of the opening, it is thus possible to calculate and implement an optimal relationship between the additional depth of focus to be provided for the eye and the amount of light (brightness) that reaches the retina.

Part of the background to the present invention can be found in the following considerations.

With the aid of ultrashort laser pulses, in particular, it is possible via multiphoton processes to induce nonlinear absorption of the laser light in materials that were originally transparent. The chemical properties of the material are permanently altered thereby, and at higher pulse energies its physical properties are also permanently altered. This nonlinear process is utilized in processes for changing the optical refractive index that are already known from the prior art and previously described, whereby the irradiated material remains transparent, however. In these aforementioned applications, the area irradiated by the laser thus remains clear and it contributes to imaging refractively or diffractively by changes in refractive power or by scattering, respectively.

It has been found, however, that the above objectives can be achieved if the material of the IOL is modified in such a way that the area irradiated and affected by the laser absorbs visible light or scatters it so strongly that hardly any light passes through this area to the retina, with preferably less than 20% of the incident light being transmitted and reaching the retina (9) of the eye.

Transforming the material from transparency to intransparency can be done photochemically, or indirectly by thermal action. The transformation process can also be carried out photo-disruptively, by which is meant that the laser treatment produces cracks or similar changes in the material, which scatter visible light strongly.

Pulses are referred to as "ultrashort" when their duration is less than one picosecond ($10^{-12}$ s).

Such disruption processes are known per se, for example, in connection with the eye, from applications such as refractive corneal surgery, in which the laser pulses make incisions in the cornea in order to create tissue flaps or to remove tissue. It is also known that ultrashort laser pulses near to or just below the disruption threshold have a photochemical effect on natural tissue and change the optical refractive index, in particular. Such mechanisms have also been used to correct refractive errors of the eye.

In these described cases, the cornea of the eye should remain optically clear after the laser procedure. In a few individual cases, a scar may form in the cornea postoperatively, resulting in optical scattering phenomena. However, this is undesirable and efforts are conventionally made to prevent such situations.

Using ultrashort pulses to fragment the graying lens and/or to open the lens capsule is known from cataract surgery.

Using ultrashort pulses to treat age-related long-sightedness (presbyopia) is also known, the ultrashort pulses cutting the lens material that has become hard with age and thus restoring the flexibility and deformability of the lens so that the lens can deform again during the accommodation process. Here, too, the aim is to administer the laser pulses in such doses that the lens remains optically clear after lasering, in order to prevent undesired dazzle.

It is known from EP 2 231 084 B1 that the laser parameters can be so designed that incident light is diffracted or dispersed at the lesions which are produced by the laser pulses and which are left behind in the lens. If a large number of such lesions are produced, it is possible by applying the principle of diffractive optics to create image-forming properties within the lens. These imaging properties can be used to correct visual defects in the eye.

In all the aforementioned applications of photodisruption to the eye, the area irradiated by the laser remains either clear and without any optical effect, or it contributes to imaging by changes in refractive power (refractive) or by scattering (diffractive). In prior art cataract surgery, the parts of the lens fragmented by the laser are removed operatively.

It has been realized in the context of the present invention that it is possible to further adapt the implanted intraocular lens by laser action, in a targeted manner and with regard to the actual situation in the eye, even when it and the eye have restabilized after the operation, such that a treated area becomes (sufficiently) intransparent to be used as an aperture. If the laser beam is programmed accordingly, it is possible, for example, for pinholes to be created in the implanted intraocular lens.

This laser-generated aperture (pinhole) can be used to block the marginal rays of the incident light by applying the principle of the stenopeic gap (pinhole effect). The marginal rays of an optical system are subject to major imaging errors (aberrations). Masking these marginal rays serves to improve the imaging quality of the eye and in particular to increase the depth of focus of the eye. When the depth of focus is increased, one is able to see objects near and far in sharp focus, even with a non-accommodating (presbyopic) eye.

In an advantageous embodiment of one aspect of the invention, the device includes an alignment unit for aligning and/or fixating the eye and a light stimulation unit for light stimulation of the eye in order to narrow the pupil, wherein the control unit is designed to control the laser unit on the basis of the narrowed pupil in order to produce marks defining the aperture opening in the lateral and/or axial direction.

In general, specifications such as "axial" and "lateral" relate to the visual axis of the eye in which the aperture is generated in the intraocular lens. "Axial" thus denotes a direction along the visual axis, whereas "lateral" denotes a direction perpendicular to the axis of vision.

In another advantageous embodiment of one aspect of the invention, the control unit is designed to control the laser unit for creating the aperture diaphragm in such a way that light transmission through the lens aperture region is reduced to 20% or less.

It has been found that complete suppression of transmission is not necessary to achieve a sufficient improvement in visual acuity, and that it is sufficient to reduce light transmission to a remainder of 20% or less. Even if greater suppression of transmission is advantageous per se and may be desirable in itself, the effort involved may be too great in the specific case to be justified by the additional benefit.

In one advantageous embodiment of one aspect of the invention, the aperture diaphragm has laser-induced modifications in multiple planes spaced axially apart. In other words, the control unit is designed to make the laser unit place the laser-induced lesions at different depths (along the visual axis of the eye).

Suppressing the transmission of light through the aperture region as completely as possible can be better achieved if the aperture extends in the axial direction over more than a single layer of modifications. The aperture diaphragm can be formed by a plurality of layers with modifications, the layers being laterally offset from one another, for example, by fractions of a periodicity of the lateral distribution of the modifications, particularly when the modifications are distributed more or less regularly inside each of them. However, axially distributing the modifications, in the form of layers or the like, is not necessary, and the modifications may also be arranged irregularly in this respect, for example, randomly, or semi-randomly at least. In extreme cases, each separate modification can be assigned its own plane.

It should be noted that the individual laser-induced modifications—at least insofar as they are arranged in a plane—do not necessarily have to be separable from each other, although a more or less contiguous modification in the form of adjacent or merging areas is possible.

In another advantageous embodiment of one aspect of the invention, the device has the laser unit for creating the aperture diaphragm in the intraocular lens implanted in the eye.

The laser unit is not necessarily integrated with the control unit in a single device, which means the control unit and the laser unit may also be provided separately so that they do not cooperate with each other until the aperture diaphragm is actually created.

In a preferred variant of the above embodiment, the laser unit includes a pulsed laser unit comprising a pulsed laser for emitting laser pulses, a focusing unit for focusing the laser pulses and an alignment unit for aligning the laser pulses, the pulsed laser being configured to emit laser pulses having a pulse duration in the range between 10,000 to 10 fs, preferably in the range between 800 and 100 fs, particularly preferably in the range between 350 and 150 fs, with a pulse energy in the range between 100 and 1 nJ, preferably in the range between 1 and 10 nJ, particularly preferably in the range between 500 nJ and 10 µJ, in the wavelength range between 400 and 1,400 nm, preferably in the range between 600 and 1,200 nm, particularly preferably in the range between 800 and 1,100 nm and with a repetition rate in the range between 1 kHz and 100 MHz, preferably in the range between 10 kHz and 10 MHz, particularly preferably in the range between 100 kHz and 5 MHz, especially preferably with a pulse duration of 150 fs, a pulse energy in the range between 10 nJ and 200 nJ, a wavelength in the range between 700 and 1100 nm and a repetition rate in the range between 100 kHz and 10 MHz.

The laser pulses can be used, on the one hand, to produce the desired modification in the intraocular lens as a whole in order to create the aperture. The control unit may also be designed, on the other hand, to control the laser unit for generating the predetermined nucleation zone by means of laser pulses, wherein the nucleation zone is formed by the material in the intraocular lens being permanently modified as a result of nonlinear absorption of a plurality of laser pulses.

The effect that results in transformation of the material can be achieved cumulatively, such that the desired local intransparency is not obtained until after a large number of laser pulses. Due to nonlinear reactions, a small amount of heat remains in the irradiated focal volume with each laser pulse applied, resulting in a corresponding local increase in temperature. This temperature increase need not have a permanent effect on the optical properties of the material, to begin with. Depending on the specific heat capacity of the irradiated material and its thermal conductivity, the temperature of the irradiated material will increase more or less when a second pulse and further pulses are applied at the same location or in immediate spatial and temporal proximity.

The spatial and temporal proximity of the second and subsequent laser pulses can now be designed in such a way that a local temperature increase occurs which results in a permanent modification of the material. This modification can be carbonization or some other chemical reaction which causes obscuration or coloring of the irradiated material, thus resulting in absorption or strong scattering of the visible light.

Unless the context indicates otherwise, the terms "obscuration zone," "coloring," or "carbonization zone" can be understood to be synonymous.

If many of these obscuration zones, each created by a large number of laser pulses, are arranged next to each other, a surface is created that can be used as an aperture diaphragm for visible light. The obscuration zones can be created pulse-wise by individual laser pulses. By placing several laser pulses close together, a contiguous darkened area can be created. The pulses may overlap in their focal volumes or may be placed greater distances apart than the focal volume, particularly if the zone of thermal influence and thus the obscuration extends beyond the focal volume.

As already mentioned above, the obscuration zones can be arranged laterally next to each other in a plane. However, it is also possible to create several planes, if the desired attenuation of the incident, more visible light is not sufficient in a given plane and too much light is still penetrating the obscuration zones.

In another preferred variant of the above embodiment, which may be combined with the above variant, the laser unit includes a laser unit for a continuous laser beam, comprising a laser source for generating a laser beam, a focusing unit for focusing the laser beam and an alignment unit for aligning the laser beam, the laser source for generating a laser beam being designed with a power level in the range between 0.1 mW and 100 W, preferably in the range between 10 mW and 10 W, particularly preferably in the range between 10 mW and 1 W, in the wavelength range between 400 and 1,400 nm, preferably in the range between 600 and 1,200 nm, particularly preferably in the range between 800 and 1,100 nm and especially preferably with a power level in the range between 10 mW to 500 mW and a wavelength in the range between 800 and 1,100 nm.

It is possible to replace the ultrashort laser pulses discussed above with longer laser pulses or even by a continuous laser beam, after obscuration zones have been introduced in a first, sufficiently large area by ultrashort laser pulses. The obscuration zones introduced by ultrashort laser pulses can be used as nucleation zones for further obscuration by delivering laser energy. As a result, the energy input (mainly thermal energy input) that is necessary can also be delivered by linear absorption at the obscuration zones that already exist. There is no longer any need for nonlinear absorption. The obscuration effect is substantially produced with the speed of heat propagation. The trajectory for completing the aperture may describe a spiral, for example, although other traces are possible.

Instead of or in addition to creating the nucleation zone by means of ultrashort laser pulses, the intraocular lens itself can be provided with a nucleation zone prior to implantation; for example, it can be doped with a small, strongly absorbent area (e.g., graphite). This area is advantageously small enough that it does not noticeably interfere with the process of seeing, as the intraocular lens is located close to the main plane of the eye as imaging system. This small area is preferably placed in such a way that, after implantation and with the pupil in its normal position (i.e., not under mydriasis/dilation of the pupil), it lies behind the pupil and not in the visual axis of the eye. The doped area can be used as a nucleation zone for further obscuration by delivery of laser energy, such that the necessary energy input (mainly thermal energy input) can also be delivered by linear absorption at the obscuration zones that already exist. There is no longer any need for nonlinear absorption. The laser exposure does not necessarily have to be pulsed any longer. Laser exposure may be continuous, instead. The obscuration effect is substantially produced with the speed of heat propagation.

The computer program according to the invention may be provided, stored, and/or sold on a suitable storage medium, for example, an optical storage medium or a non-volatile electronic storage medium. It may also be provided in conjunction with or as part of a hardware component. The computer program may also be provided in other ways, such as via the Internet or by wired or wireless means of telecommunication.

Features of advantageous embodiments of the invention are defined in the dependent claims, in particular, and a person skilled in the art can also find other advantageous features, embodiments and variants of the invention in the above description and the discussion below.

BRIEF DESCRIPTION OF THE DRAWINGS

In the following, the present invention shall be illustrated and described with reference to the embodiments shown in the Figures, in which.

DETAILED DESCRIPTION OF THE EMBODIMENTS

In the enclosed drawings and in the associated descriptions of said drawings, corresponding or related elements are given corresponding or similar reference signs, where expedient, even when they are to be found in different embodiments.

As discussed above, FIG. 1a and FIG. 1b show clearly the increased depth of focus effect produced by a pinhole. An IOL 2 optimized for distance vision and implanted in eye 1 focuses a parallel incident beam from distance 3 onto the retina of the eye 9 with a short depth of focus 5a. Due to the insufficient refractive power of IOL 2, the light from an object at close range 4 is imaged behind retina 9 with a similarly short depth of focus 5b.

If the entrance opening for the incident light 3 and 4 is constricted by an aperture 6, the depth of focus 7 for imaging is preferably so wide that sufficiently sharp imaging on retina 9 occurs both for near objects 4 and for light 3 incident from a distance.

FIGS. 2a and 2b show schematic views of an intraocular lens 2 with an aperture 6, FIG. 2a showing a cross-sectional view of an example of an embodiment of a laser-induced aperture 6 within an IOL 2 and FIG. 2b showing a top view of an example of an embodiment of a laser-induced aperture 6 within an IOL 2.

Figure 3A:
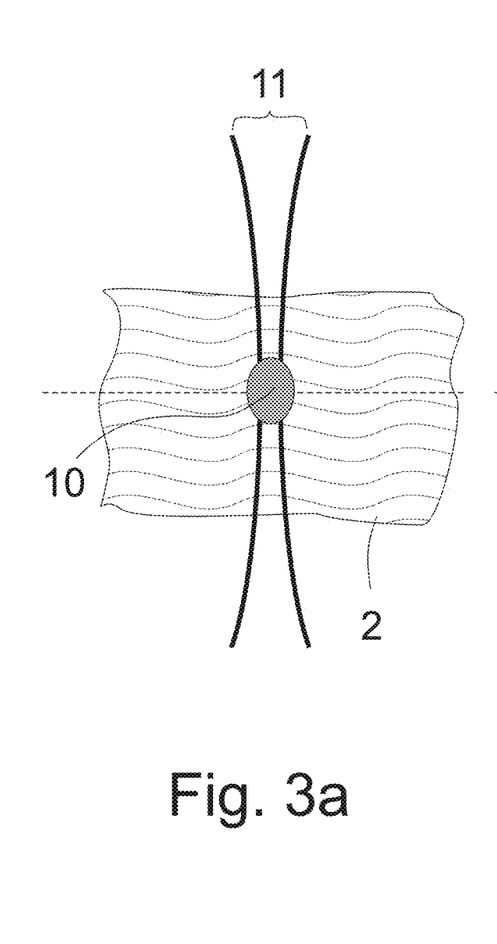
FIGS. 3a-3c show schematic views for describing the flow of temperature into intraocular lens material.
Figure 3B:
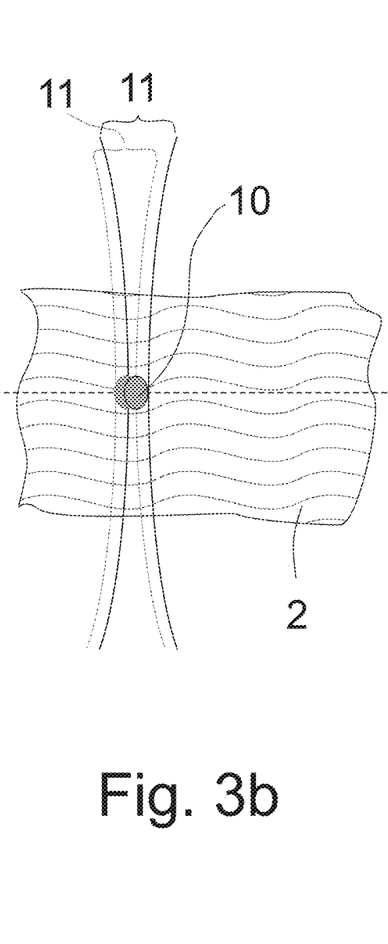
Figure 3C:
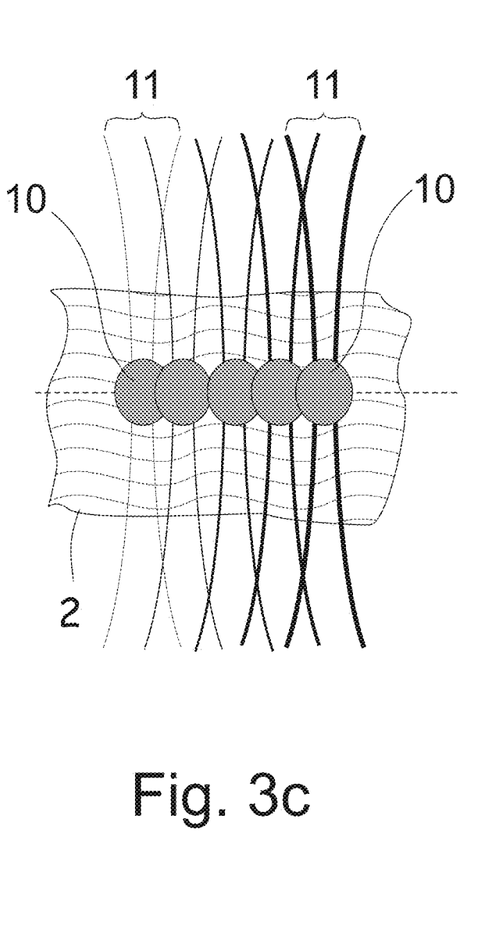

FIGS. 3a-3c show schematic views for describing the flow of temperature into intraocular lens material.

By providing a suitable laser pulse 11, an obscuration zone 10 can be created in the material of intraocular lens 2, as illustrated in FIG. 3a. If a plurality of laser pulses 11 are placed close together, as illustrated in FIG. 3b, it is possible to create a contiguous area of obscuration. The focal volumes of the pulses may overlap. If the zone of thermal influence and thus the obscuration zone 10 produced by laser pulse 11 extends beyond the focal volume, laser pulses 11 can be placed further apart than the focal volume, as illustrated in FIG. 3c.

Figure 4A:
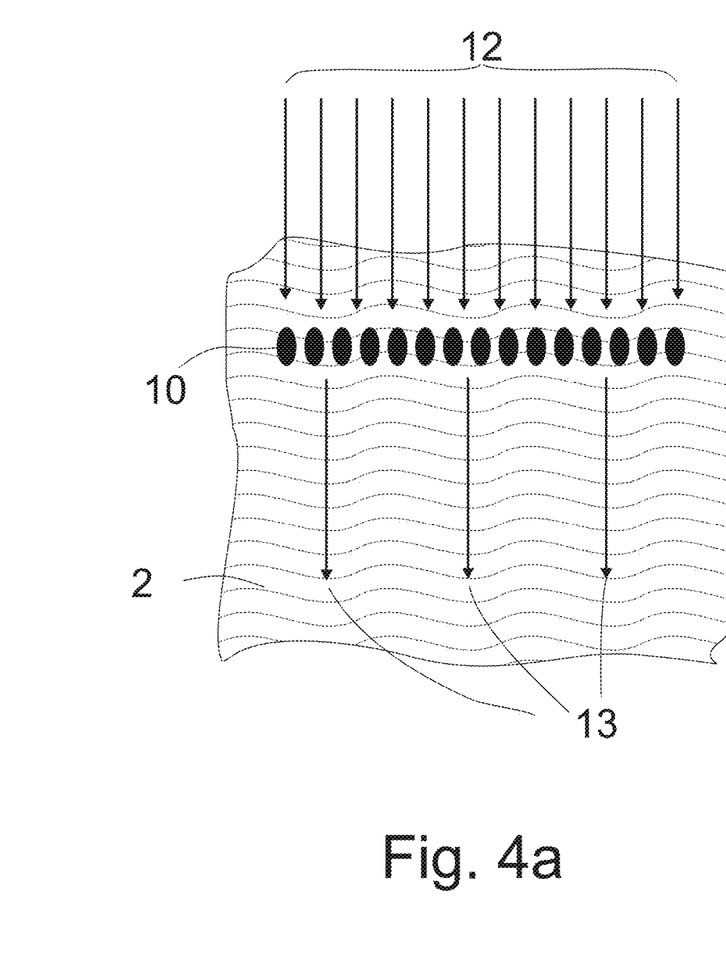
FIGS. 4a and 4b show schematic views for comparing transmission with a single-layer arrangement of modifications and with a multi-layered arrangement of modifications.
Figure 4B:
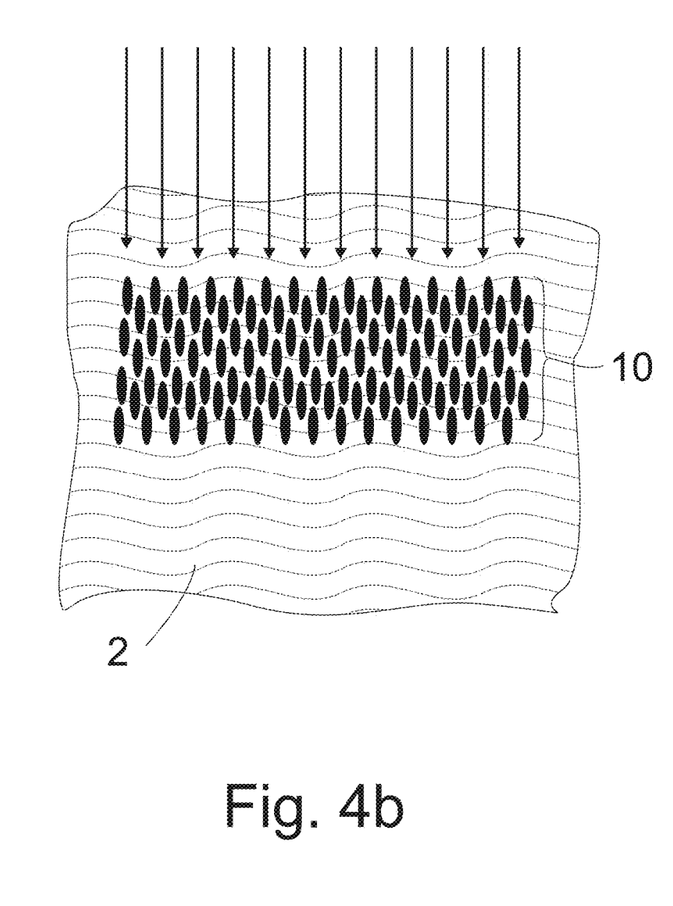

FIGS. 4a and 4b show schematic views for comparing transmission with a single-layer arrangement of modifications and with a multi-layered arrangement of modifications. A single-layer arrangement of obscuration zones (or general modifications) 10 within intraocular lens 2 may, as in this example, result in incident light 12 mainly being scattered or absorbed in all directions. Even when the lateral arrangement of obscuration zones or modifications 10 is very dense, what is still a substantial proportion of the incident light may be scattered forwards (13) and may thus reach the retina 9. In contrast, a plurality of layers of laterally closely-packed obscuration zones or modifications 10, as illustrated in FIG. 4b, will reduce the likelihood of photons being scattered in the direction of the retina 9.

If, as envisaged by the present invention, as little light as possible is to pass through the aperture region (surrounding the aperture opening), the obscuration zones or modifications 10 must be arranged as close as possible laterally. If some of the obscuration zones or modifications 10 happen not to absorb the light, but merely scatter it, some of the incident light 3, 4 may nevertheless scatter forwards and thus reach the retina 9, even when the obscuration zones or modifications 10 are arranged laterally very close together (FIG. 4*a*). The scattered photons that reach the retina 9 do not contribute to image formation and are perceived as annoying. Contrast vision, in particular, is adversely affected as a result.

If, on the other hand, a plurality of layers of laterally densely packed obscuration zones or modifications 10 are also created in the axial direction, then the probability of photons being scattered towards the retina 9 becomes increasingly smaller. Once there is a certain thickness or quantity of successive layers, the amount of transmitted light is so small, even without any further special measures regarding the design of the obscuration zones or modifications 10, that the contrast is reduced to only an insignificant or acceptable extent during image formation on the retina 9 (FIG. 3*b*).

For reasons of uniformity alone, obscuration zones or modifications 10 are preferably placed side by side in one plane. If the desired attenuation of the incident, more visible light 12 achieved by creating one plane of obscuration zones or modifications 10 is not yet sufficient and too much light 13 still passes through the obscuration zones or modifications 10, a plurality of planes may be created one above the other.

Figure 5A:
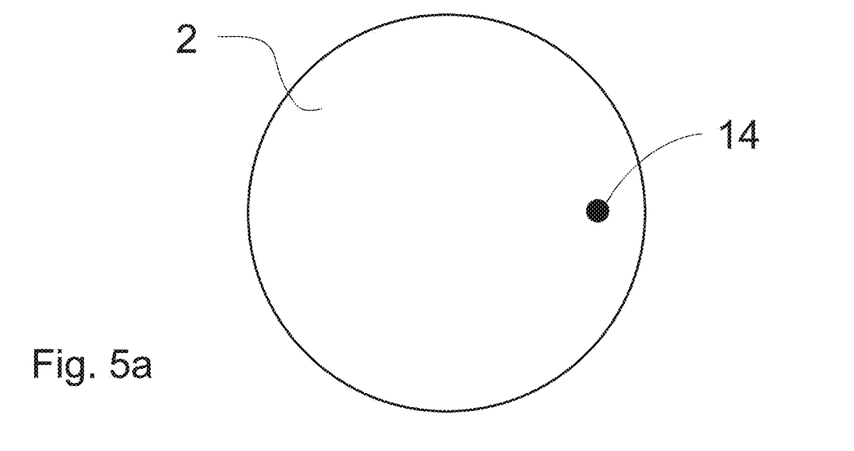
FIGS. 5a-5c show schematic views illustrating the procedure of creating an aperture in the implanted intraocular lens.
Figure 5B:
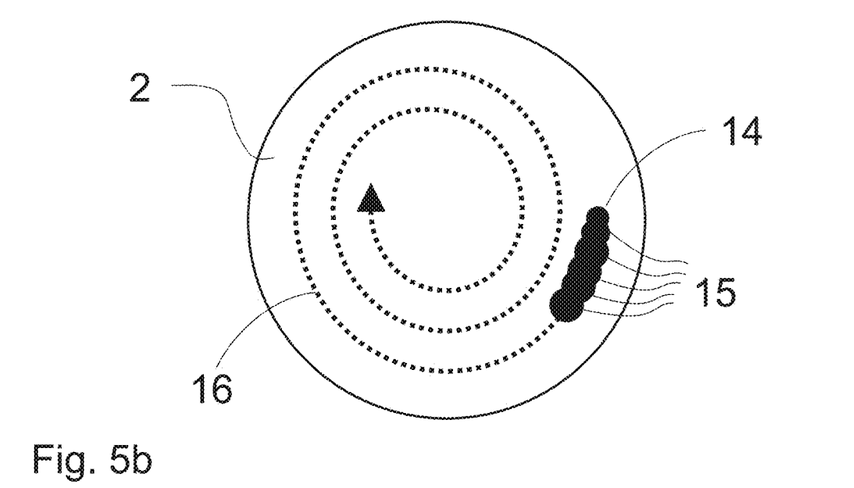
Figure 5C:
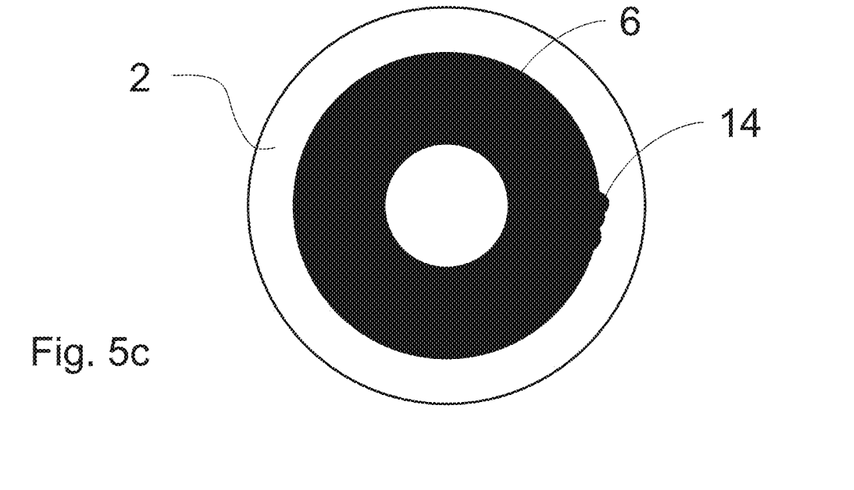

FIGS. 5*a*-5*c* show schematic views illustrating the procedure of creating an aperture in the implanted intraocular lens.

FIG. 5*a* shows an (implanted) intraocular lens 2 with a nucleation zone 14. Within the scope of the invention, it is possible that this nucleation zone 14 is created by one, a few, or even by many ultrashort laser pulses as a result of nonlinear absorption, whereby the nucleation zone 14 is already provided in the intraocular lens 2 prior to implantation, for example, by doping with graphite or the like. These approaches can also be combined, and it is equally possible that the nucleation zone 14 is already created by laser action prior to implantation.

Following the situation shown in FIG. 5*a*, and as indicated in FIG. 5*b*, longer laser pulses 15 or even continuous laser irradiation can subsequently use the obscuration zones or modifications 10 as a nucleation zone 14 in order to heat the material further by linear absorption and to create an aperture 6, for example, by describing a spiral trajectory 16, as illustrated in finished form in FIG. 5*c*.

FIGS. 6*a*-6*d* show schematic views for describing procedures for creating an aperture according to the invention with previous marking.

Figure 6A:
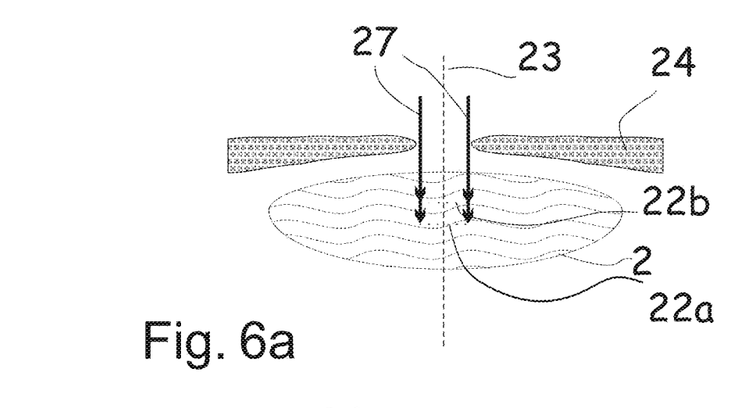
FIGS. 6a-6d show schematic views for describing procedures for creating an aperture diaphragm according to the invention with previous marking.
Figure 6B:
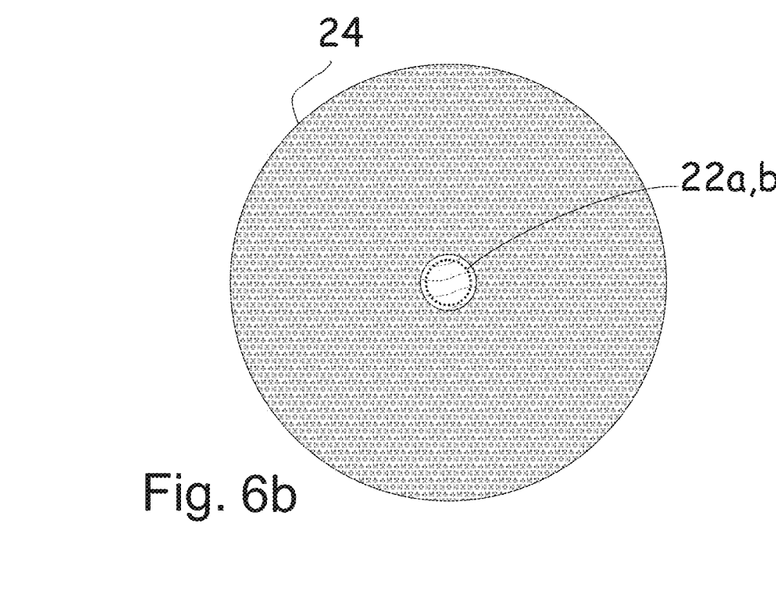

As shown in FIG. 6*a*, one or more orientation points 22*a*, 12*b* can be lasered into intraocular lens 2 with the aid of laser beam 27 while the pupil is narrow (miosis). These can be two rings, for example, indicating the posterior position (22*a*) and anterior position (22*b*) of the aperture opening. The lateral position of the marks is limited by the inner edge of the iris 24. FIG. 6*b* shows the same situation as in FIG. 6*a* from the operator perspective (top view).

Figure 6C:
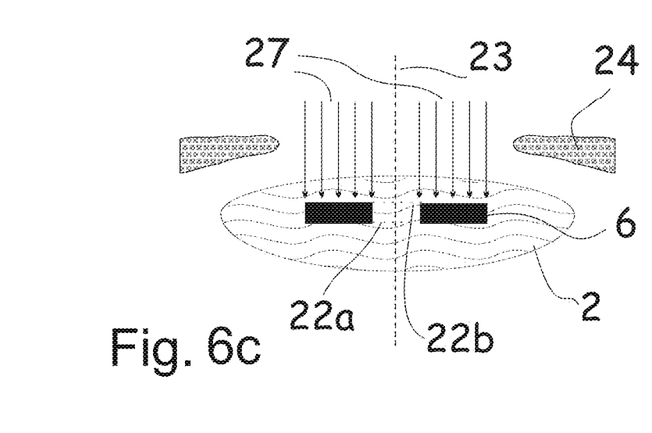
Figure 6D:
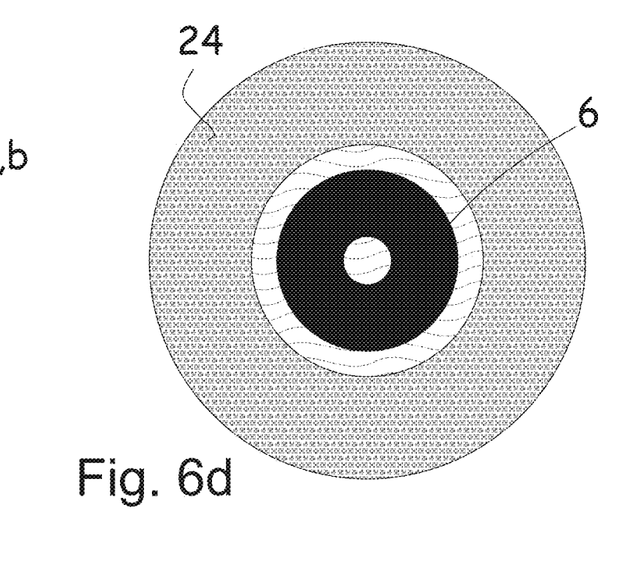

FIG. 6*c* shows how, when the pupil is dilated (mydriasis), the entire aperture 6 can be lasered into intraocular lens 2 without the iris 24 blocking the beam path of laser 27. The previously placed marks 22*a*, 22*b* help to center the aperture accordingly and to orient it along the visual axis 23. FIG. 6*d* shows the same situation as in FIG. 6*c* from the operator perspective (top view).

The laser-generated aperture can be centered and oriented in relation to the visual axis of the eye. It is advantageous, for example, to position the center of the aperture in the middle between the center of the pupil and the "first Purkinje reflection." If the pupil needs to be dilated by medication during laser application (mydriasis), it is advantageous if a mark is first applied to the surface of the cornea, for example, with dye, when the pupil is narrowed.

Advantageous positioning results from centering and orientation at the iris 24 when the pupil is narrow (miosis). After the patient's eye has been aligned with the laser apparatus and fixated, if necessary, for example, by means of a commonly used "patient interface," the eye is stimulated by comparatively bright light. The eye consequently adapts by narrowing the pupil (miosis). In this situation, one or more orientation points 22*a*, 22*b* can be lasered into lens 2 by laser 27; for example, two rings indicating the posterior and anterior positions of the aperture opening (FIGS. 6*a*, 6*b*). Positioning can be supported by standard imaging techniques such as optical coherence tomography (OCT).

Once the marks have been placed, the light stimulus is removed. The eye, or both the patient's eyes, are preferably left in maximum darkness. The eye will consequently adapt once again to the light conditions and will dilate the pupil (mydriasis). In this situation, the entire aperture 6 can now be lasered into lens 2 without the iris 24 blocking the beam path of the laser. The previously placed marks 22*a*, 22*b* help to center the aperture accordingly and to orient it along the visual axis 23. If natural mydriasis is not sufficient to move the iris 24 completely out of the beam path of laser 27, further mydriasis can be induced by medication. The advantage of this approach is that, after the laser procedure, in bright daylight, the naturally narrowed, adapted pupil matches the opening of the laser-generated aperture.

Even if different aspects or features of the invention are shown in combination in the Figures, it is clear to a person skilled in the art, unless otherwise specified, that the combinations shown and discussed are not the only ones possible. More particularly, it is possible to swap corresponding units or groups of features from different embodiments.

It should be noted that the mask/aperture to be created in the IOL does not necessarily have to be a circular aperture. The shape of the aperture can be adapted, rather, to the visual defect to be corrected. If the visual defect is astigmatism, the aperture opening can be made smaller in the axis in which there is astigmatism than in the axis in which there is no visual defect.

In implementations of the invention, individual components, such as a processor, may wholly or partly assume the functions of various elements mentioned in the claims. Procedures or processes such as controls, calculations, measurements, or similar may be implemented as programming means of a computer program and/or as special hardware components.

The invention claimed is:

1. A device for creating an aperture diaphragm in an artificial intraocular lens implanted into an eye, said device comprising:
   a control unit for a laser unit;
   wherein the control unit is designed to control the laser unit to create the aperture diaphragm in the intraocular lens, wherein the aperture diaphragm is used to increase the depth of focus of the eye and is formed by laser-induced modification of the material of the intraocular lens, which reduces light transmission through an intraocular lens aperture region surrounding an aperture opening; and wherein the control unit is designed to control the laser unit in such a way that creation of the aperture diaphragm starts from a predetermined nucleation zone in the intraocular lens;

wherein the laser unit creates the aperture diaphragm in the intraocular lens implanted in the eye;

wherein the laser unit includes a pulsed laser unit comprising a pulsed laser for emitting laser pulses, a focusing unit for focusing the laser pulses, and an alignment unit for aligning the laser pulses; and wherein the pulsed laser is configured to emit laser pulses having a pulse duration of 150 fs, a pulse energy in the range between 10 nJ and 200 nJ, a wavelength in the range between 700 and 1100 nm and a repetition rate in the range between 100 kHz and 10 MHz.

2. The device according to claim 1, the device further comprising:
an alignment unit for aligning and/or fixating the eye; and
a light stimulation unit for light stimulation of the eye in order to narrow the pupil;
wherein the control unit is designed to control the laser unit on the basis of the narrowed pupil in order to produce marks defining the aperture opening in the lateral and/or axial direction.

3. The device according to claim 1, wherein the control unit is designed to control the laser unit for creating the aperture diaphragm in such a way that light transmission through the intraocular lens aperture region is reduced to 20% or less.

4. The device according to claim 1, wherein the aperture diaphragm has laser-induced modifications in a plurality of levels that are spaced apart from one another in an axial direction.

5. The device according to claim 1 wherein the pulsed laser is configured to emit laser pulses having a pulse duration in the range between 10,000 to 10 fs, with a pulse energy in the range between 100 and 1 nJ, in the wavelength range between 400 and 1,400 nm, and with a repetition rate in the range between 1 kHz and 100 MHz.

6. The device according to claim 1, wherein the laser unit includes a laser unit for a continuous laser beam, comprising a laser source for generating a laser beam, a focusing unit for focusing the laser beam, and an alignment unit for aligning the laser beam.

7. The device according to claim 1, wherein the laser source for generating a laser beam is designed with:
a power level in the range between 0.1 mW and 100 W and a wavelength range between 400 and 1,400 nm.

8. The device according to claim 1, wherein the laser source for generating a laser beam is designed with:
a power level in the range between 10 mW to 500 mW and a wavelength in the range between 800 and 1,100 nm.

9. The device according to claim 1, wherein the control unit is designed to control the laser unit for generating the pre-determined nucleation zone by means of laser pulses, wherein the nucleation zone is formed by the material in the intraocular lens being permanently modified as a result of nonlinear absorption of a plurality of laser pulses.

10. An intraocular lens for implantation in an eye, said intraocular lens comprising:
a predetermined nucleation zone in the intraocular lens, wherein the nucleation zone is configured for linear absorption of energy delivered by a laser unit;

wherein the laser unit creates the aperture diaphragm in the intraocular lens implanted in the eye;

wherein the laser unit includes a pulsed laser unit comprising a pulsed laser for emitting laser pulses, a focusing unit for focusing the laser pulses, and an alignment unit for aligning the laser pulses; and wherein the pulsed laser is configured to emit laser pulses having a pulse duration of 150 fs, a pulse energy in the range between 10 nJ and 200 nJ, a wavelength in the range between 700 and 1100 nm and a repetition rate in the range between 100 kHz and 10 MHz.

11. The intraocular lens according to claim 10, wherein the nucleation zone is spaced apart from a visual axis of the intraocular lens, wherein the nucleation zone is preferably provided in a region of the intraocular lens that is located posterior to the pupil when the intraocular lens is implanted and the pupil is in its normal position.

12. A method of generating control commands for a laser unit for creating an aperture diaphragm in an intraocular lens implanted in an eye, the method comprising the steps of:
generating the control commands to cause the laser unit to create the aperture diaphragm in the intraocular lens, wherein the aperture diaphragm is used to increase the depth of focus of the eye and is formed by laser-induced modification of the material of the intraocular lens, which reduces light transmission through an intraocular lens aperture region surrounding an aperture opening;
wherein the control commands cause the laser unit to control the laser unit in such a way for creation of the aperture diaphragm that creation of the aperture diaphragm starts from a predetermined nucleation zone in the intraocular lens;
wherein the laser unit creates the aperture diaphragm in the intraocular lens implanted in the eye;
wherein the laser unit includes a pulsed laser unit comprising a pulsed laser for emitting laser pulses a focusing unit for focusing the laser pulses, and an alignment unit for aligning the laser pulses; and
wherein the pulsed laser is configured to emit laser pulses having a pulse duration of 150 fs, a pulse energy in the range between 10 nJ and 200 nJ, a wavelength in the range between 700 and 1100 nm and a repetition rate in the range between 100 kHz and 10 MHz.

13. A method of creating an aperture diaphragm in an artificial intraocular lens implanted into an eye, the method comprising the steps of:
controlling a laser unit to create the aperture diaphragm in a lens of the eye, wherein the aperture diaphragm is used to increase the depth of focus of the eye and is formed by laser-induced modification of the material of the intraocular lens, which reduces light transmission through an intraocular lens aperture region surrounding an aperture opening;
wherein the laser unit is controlled in such a way that creation of the aperture diaphragm starts from a pre-determined nucleation zone in the intraocular lens;
wherein the laser unit creates the aperture diaphragm in the intraocular lens implanted in the eye;
wherein the laser unit includes a pulsed laser unit comprising a pulsed laser for emitting laser pulses a focusing unit for focusing the laser pulses, and an alignment unit for aligning the laser pulses; and
wherein the pulsed laser is configured to emit laser pulses having a pulse duration of 150 fs, a pulse energy in the range between 10 nJ and 200 nJ, a wavelength in the range between 700 and 1100 nm and a repetition rate in the range between 100 kHz and 10 MHz.

14. A computer program for controlling a device comprising:
- a control unit for a laser unit;
- wherein the control unit is designed to control the laser unit to create the aperture diaphragm in the intraocular lens, wherein the aperture diaphragm is used to increase the depth of focus of the eye and is formed by laser-induced modification of the material of the intraocular lens, which reduces light transmission through an intraocular lens aperture region surrounding an aperture opening;
- wherein the control unit is designed to control the laser unit in such a way that creation of the aperture diaphragm starts from a predetermined nucleation zone in the intraocular lens; and
- wherein the computer program causes the device to create the aperture diaphragm in the artificial intraocular lens implanted into an eye, when the computer program is executed on the device;
- wherein the laser unit creates the aperture diaphragm in the intraocular lens implanted in the eye;
- wherein the laser unit includes a pulsed laser unit comprising a pulsed laser for emitting laser pulses, a focusing unit for focusing the laser pulses, and an alignment unit for aligning the laser pulses; and
- wherein the pulsed laser is configured to emit laser pulses having a pulse duration of 150 fs, a pulse energy in the range between 10 nJ and 200 nJ, a wavelength in the range between 700 and 1100 nm and a repetition rate in the range between 100 kHz and 10 MHz.

* * * * *